United States Patent
Nygaard

(10) Patent No.: US 6,542,833 B1
(45) Date of Patent: Apr. 1, 2003

(54) METHOD OF CHECKING THE PERFORMANCE OF A FLOW CYTOMETER INSTRUMENT AND APPARATUS FOR EXECUTING SAID METHOD AS WELL AS A STANDARD KIT THEREFORE

(75) Inventor: Lars Nygaard, Græsted (DK)

(73) Assignee: Foss Electric A/S, Hillerod (DK)

( * ) Notice: Subject to any disclaimer, the term of this patent is extended or adjusted under 35 U.S.C. 154(b) by 0 days.

(21) Appl. No.: 09/508,437

(22) PCT Filed: Sep. 14, 1998

(86) PCT No.: PCT/DK98/00389

§ 371 (c)(1),
(2), (4) Date: Mar. 10, 2000

(87) PCT Pub. No.: WO99/14574

PCT Pub. Date: Mar. 25, 1999

(30) Foreign Application Priority Data

Sep. 12, 1997 (DK) .............................................. 1053/97

(51) Int. Cl.[7] .................................................. G01F 1/00
(52) U.S. Cl. ....................................................... 702/46
(58) Field of Search ........................ 702/45, 46; 436/8, 436/10, 23, 52, 172

(56) References Cited

U.S. PATENT DOCUMENTS

| | | |
|---|---|---|
| 4,767,206 A | 8/1988 | Schwartz |
| 4,774,189 A | 9/1988 | Schwartz |
| 4,867,908 A * | 9/1989 | Recktenwald et al. ........ 436/10 |
| 4,918,004 A | 4/1990 | Schwartz |
| 5,073,497 A | 12/1991 | Schwartz |
| 5,084,394 A | 1/1992 | Vogt et al. |
| 5,093,234 A | 3/1992 | Schwartz |
| 5,380,663 A | 1/1995 | Schwartz et al. |
| 6,177,277 B1 * | 1/2001 | Soini ........................... 436/172 |
| 6,183,697 B1 * | 2/2001 | Tanaka et al. ........... 422/82.05 |

FOREIGN PATENT DOCUMENTS

| | | |
|---|---|---|
| EP | 0335001 A2 | 10/1989 |
| EP | 0421736 A2 | 4/1991 |
| WO | WO 9707390 | 2/1997 |

* cited by examiner

*Primary Examiner*—Judy Nguyen
(74) *Attorney, Agent, or Firm*—Birch, Stewart, Kolasch & Birch, LLP

(57) ABSTRACT

A method for correcting the settings of a flow cytometer, designed for fast sample handling and counting, allowing about 500 samples per hour to be counted. The counting is based on the provision of data representing a PHA diagram (Pulse Height Analysis) of registered pulses, each indicating a passed cell or particle. To check the settings the user measures a standard sample of uniform microbeads 161 on the flow cytometer, and inserts information on a disk 162 in a computer arranged to process the measured data and to calculate: a plurality of particle counts on the same sample, a mean count, a standard deviation s and/or Coefficient of Variation CV, a signal mean value SM, a signal width (width of the bell-curve in the PHA-diagram). The parameters are compared to pre-set limits (165, 166, 167, 168) and the PHAS curve is compared to an ideal curve PHA0. A user help program for adjusting the flow cytometer is arranged to display typical symptoms on a computer screen, to indicate the possible defects and to recommend actions to remedy the problems, based on information in a library stored in the computer. Thereby a visit by a service engineer can often be avoided.

14 Claims, 9 Drawing Sheets

Fossomatic Quality Check - View FMA samples

| Man | | | | 1 - Results | | | | 2 - Graphs | | 3 - PHA |
|---|---|---|---|---|---|---|---|---|---|---|
| | Date | Time | Count | CV | R | Signal Mean | CV | Signal Width | Remarks | Lot | Gain |
| 52 | 11.07.97 | 13:22:47 | 392 | 2.18 | 2.76 | 59 | 1.0 | 8 | Prof. bas | 7144511 | 615 |
| 53 | 10.07.97 | 17:34:39 | 389 | 6.69 | 2.77 | 68 | 0.0 | 8 | OK | 7144511 | 615 |
| 54 | 12.07.97 | 09:25:52 | 398 | 0.69 | 2.74 | 64 | 0.9 | 8 | OK | 7144511 | 615 |
| 55 | 12.07.97 | 11:26:19 | 393 | 1.11 | 2.76 | 67 | 0.9 | 8 | OK | 7144511 | 615 |
| 56 | 12.07.97 | 13:48:49 | 394 | 0.95 | 2.75 | 67 | 0.9 | 8 | OK | 7144511 | 615 |
| 57 | 15.07.97 | 06:51:50 | 398 | 2.47 | 2.74 | 67 | 0.9 | 8 | OK | 7144511 | 615 |
| 58 | 15.07.97 | 08:52:45 | 405 | 2.71 | 2.71 | 67 | 0.0 | 8 | OK | 7144511 | 615 |
| 59 | 15.07.97 | 10:54:27 | 388 | 2.69 | 2.77 | 67 | 1.0 | 8 | OK | 7144511 | 615 |
| 60 | 15.07.97 | 13:00:11 | 387 | 1.83 | 2.78 | 67 | 0.9 | 8 | OK | 7144511 | 615 |
| 61 | 16.07.97 | 15:07:45 | 393 | 3.02 | 2.76 | 65 | 0.0 | 8 | OK | 7144511 | 615 |
| 62 | 17.07.97 | 17:55:21 | 394 | 1.36 | 2.75 | 68 | 0.0 | 9 | OK | 7144511 | 615 |
| 63 | 17.07.97 | 06:24:36 | 385 | 4.15 | 2.79 | 67 | 0.9 | 8 | OK | 7144511 | 615 |
| 64 | 17.07.97 | 08:19:13 | 395 | 2.04 | 2.75 | 67 | 0.9 | 8 | OK | 7144511 | 615 |
| 65 | 17.07.97 | 10:17:52 | 387 | 1.54 | 2.78 | 63 | 1.6 | 8 | OK | 7144511 | 615 |
| 70 01 | 18.07.97 | | | | | | | | | | |

Lot 7144511 data

| | Value | Low limit | High limit |
|---|---|---|---|
| Particles | 396 | 371 | 421 |
| Signal Mean | 73 | 62 | 81 |
| Use before | 970901 | | |

Result details for 58

| | Count | R | Signal Mean | Signal Width | Z | Discriminator | Noise Level | Remarks |
|---|---|---|---|---|---|---|---|---|
| rep 1 | 418 | 2.67 | 58 | 8 | 3.3 | 29 | 4 | Prof bas |
| rep 2 | 399 | 2.74 | 58 | 8 | 3.4 | 28 | 4 | Prof bas |
| rep 3 | 399 | 2.73 | 58 | 8 | 3.7 | 25 | 4 | Prof bas |
| Average | 405 | 2.71 | 58 | 8 | 3.4 | 27 | 4 | Prof bas |
| CV [%] | 2.71 | | 0.0 | | | | | |
| Lot Average | 396 | 2.75 | 73 | | | | | |

*Fig. 9*

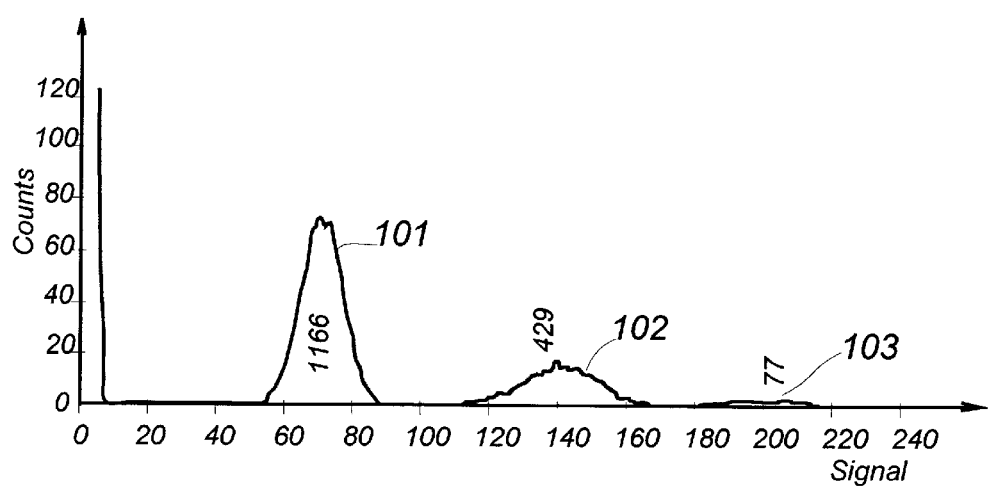

*Fig. 15*

METHOD OF CHECKING THE PERFORMANCE OF A FLOW CYTOMETER INSTRUMENT AND APPARATUS FOR EXECUTING SAID METHOD AS WELL AS A STANDARD KIT THEREFORE

This application is the national phase under 35 U.S.C. §371 of PCT International Application No. PCT/DK98/00389 which has an International filing date of Sep. 14, 1998, which designated the United States of America.

TECHNICAL FIELD

The present invention concerns a new method of checking the performance of a flow cytometer, the flow cytometer comprising means delivering electrical pulse signals indicating the presence of particles, such as somatic cells or bacteria. The invention is specifically dedicated to milk testing and more specifically to determination of the number of somatic cells in milk. Further according to the present invention the method allows for inspection and correction for any agglomeration of particles in a standard sample used for checking the performance of the flow cytometer. Further the invention concerns an apparatus comprising data processing equipment arranged to execute the above method, as well as a stannard kit for application in the apparatus.

BACKGROUND ART

Flow cytometers are instruments used for analysis of particles suspended in a fluid, e.g. biological cells in body fluids, such as somatic cells in milk. Briefly, a flow cytometer comprises a liquid flow system and an optical system intersecting each other in a flow cuvette, as well as an electronic system, detecting fluorescence or scatter originating from particles passing through the cuvette. Preferably, the fluid sample flows in a single, thin string inside the cuvette thereby allowing any particles present to be counted one by one. Further, in a preferred embodiment the thin string is surrounded by a sheath fluid. Thanks to the sheath fluid, casual impurities, present in the fluid and having a size larger than the particles or cells to be counted and accordingly larger than the size of the string of fluid sample, will not cause clogging. They might have done so if flowing in a liquid channel as narrow as the thin inner string.

The method according to the invention is specifically developed for flow cytometers applied for fast determination of the number of cells in a milk sample or a milk product and more specifically for the fluorescent type of flow cytometers, in which the cells or particles are all stained by a fluorescent dye, which reacts fluorescent when exposed to illumination. A fluorescence signal of adequate size, i.e. above noise, is considered to indicate the passage of a particle or cell. In the preferred embodiment of the flow cytometer, the presently preferred agent or dye is Ethidium Bromide. The present type of flow cytometer has only one channel, i.e. it is optimised to detect only one kind of fluorescence or scatter. However, flow cytometers may have a plurality of channels, each dedicated to a specific dye.

The somatic cell count is considered a measure of the milk quality (high quality milk has a low cell count). Accordingly the cell count can be applied by the dairy when setting the price according to which the farmer is paid for the delivered milk. In order to ensure correct payment to the farmer and to reveal any milk of too low quality, a proper functioning of the flow cytometer is crucial.

In order to obtain accurate and reproducible results flow cytometers must be aligned and calibrated. The light ray from the illumination source must hit the stream of particles and the detector optics must focus on the particle stream when the illuminated particles exhibit fluorescence. Also the gain and characteristics of the electronic circuits processing the detected signals and the applied mathematics must produce a number indicating the true number of particles in the stream with a sufficient accuracy and reproducibility.

Possible Reasons for Poor Performance

Any defects or maladjustment of flow rates (or clogging) in the flow system and/or defects or misalignment of the optical system may cause the count to either decrease or increase compared to the true value.

Prior Art

U.S. Pat. No. 5,093,234 (Schwartz) discloses a method of aligning, compensating and calibrating a flow cytometer for analysis of samples and a microbead standard kit therefore. The method can be applied to multi-channel flow cytometers. The method includes running test measurements on standard kits; adjusting fluorescence channel PMT voltages and gain to position resulting dot plot or histogram near the origin of the axis of each of the fluorescence channels; and setting boundary levels in each channel to indicate fluorescence intensity. The standard kit comprises a blank and/or an auto-fluorescent microbead population and at least two series of calibrated microbead populations labelled with fluorescent dye(s). U.S. Pat. No. 5,084,394 (Vogt et al) discloses a similar method for corrective calibration of a flow cytometry using a mixture of fluorescent microbeads and cells. These methods provide for an advanced, sophisticated and qualitative analysis of single cells such as lymphocytes in blood.

The present method concerns a "performance check", i.e. a monitoring of functional performance, of a single channel flow cytometer for counting somatic cells in milk. The instrument is specifically designed for fast sample handling and counting, allowing about 500 samples pr hour to be counted. This kind of flow cytometer counts the cells based upon measuring only one parameter, such as green or red fluorescence. The instrument is not intended for qualitative studies of the cells. The performance check method is based on the use of a standard and/or calibration fluid comprising only one type of particles or microbeads which are unstained until they enter the process according to the present invention. Thereby the standard fluid samples are as simple as possible. The standard samples are very stable and adequate for a long term shelf life, i.e. a great number of standard samples may be stored by the user for months or years for future use, such as a regular performance check every morning or when ever necessary.

Besides a thorough check of the operation of the flow cytometer the standard fluid could also be applied for a calibration of the flow cytometer.

SUMMARY OF THE INVENTION

The present invention provides a method of checking the performance of a flow cytometer instrument, in which instrument the number of particles or cells in a fluid flow are counted by providing data representing a PHA diagram (Pulse Height Analysis), of registered pulses. The invention is characterised by—providing a lot of standard samples, including only one type of substantially uniform microbeads,—providing data representing an optimal (desired) PHA diagram (PHA0) of the pulses registered, when measuring a standard sample from the lot on a reference instrument, said data being stored in a memory in the instrument itself, or a memory in data processing means connected to the instrument, or in means from which the data may be imported into the instrument or into the data processing means connected to the instrument,—measuring a standard sample on the instrument to be checked,—providing data representing a PHA diagram (PHAS) for the pulses registered during the measurement of the standard sample on the instrument to be checked,—comparing the present PHA diagram (PHAS) to the optimal PHA diagram (PHA0),—and analysing and/or evaluating said data in order to determine any poor or faulty operation of the instrument. By this method the user can check the instrument regularly, and the user can readily be informed of any precautions to be taken. Preferably the microbeads in the lot are unstained until the enter the instrument. The use of unstained microbeads are specific favourable in that also the staining process in the instrument is controlled when measuring the standard sample.

Preferably at least one of the following parameters are calculated: a particle count, a plurality of particle counts on the same sample, a standard deviation, s, and/or Coefficient of Variation, CV, based on (at least two, preferably three) repeated/consecutive measurements on the same sample and substantially at the same time, a signal mean value, and a signal width, i.e. the width of the bell-curve in the PHA-diagram—the corresponding data for the standard sample of the standard fluid measured on a reference instrument. i.e. the optimum values of said data, being provided with the lot—comparing at least one of the above parameters for the actual measurement of standard sample to the corresponding optimal parameters of the standard fluid,—and analysing said data to estimate whether the instrument is operating substantially optimally, (i.e. within preferred limits) or is not operating substantially optimally (i.e. outside preferred limits), registering any off-limit deviations from optimal operation.

Preferably the registered off-limit deviations are considered as symptoms which are displayed to the user.

Preferably the data processing equipment comprises means for evaluating the observed symptoms, proposing possible defects (make a diagnosis), and making recommendations for how to remedy any poor performance, and/or any precautions to be taken. Preferably the means for evaluating the symptoms include a library stored in memory means arranged to be accessed by the data processing means. Preferably, the means for checking the performance/evaluating the symptoms includes display of a list of consecutive results to the user on a monitor and/or providing a print out. Preferably, the means for checking the performance/evaluating the symptoms includes display of detailed results and data of recent measurements of the standard fluid. Preferably the means for checking the performance/evaluating the symptoms includes displaying a measured PHA—diagram on request from the user.

Preferably the means for checking the performance/evaluating the symptoms includes display of a list of possible situations comprising defined symptoms and for each situation present information on possible reasons and appropriate actions to remedy the defect.

The display of any symptoms and actions to remedy any default operation is advantageous in that the user himself will be able to adjust the instrument to obtain optimum performance. Thereby the visit by a service engineer can be avoided. Thereby the loss of precious measurement time due to poor performance is avoided.

The apparatus according to the invention is arranged to execute the above method. The standard kit according to the invention comprises a standard fluid including a plurality of substantially uniform microbeads and associated means carrying information on the lot, and specifically on the content of microbeads in the standard fluid.

The method and kit is specifically favourable in that the test samples (standard samples) are handled in the same way as any other sample, and any defect in the instrument, which is liable to influence an ordinary measurement result will also be liable to in influence the result of the test measurement on the standard sample.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 9 shows a screen print displaying three "windows", 1) a list of result, 2) result details, and 3) lot data, as the screen print may appear unclear all data are listed in tables in the text.

FIG. 15 shows a PHA-diagram indicating agglomeration of particles.

Figures 10, 11:
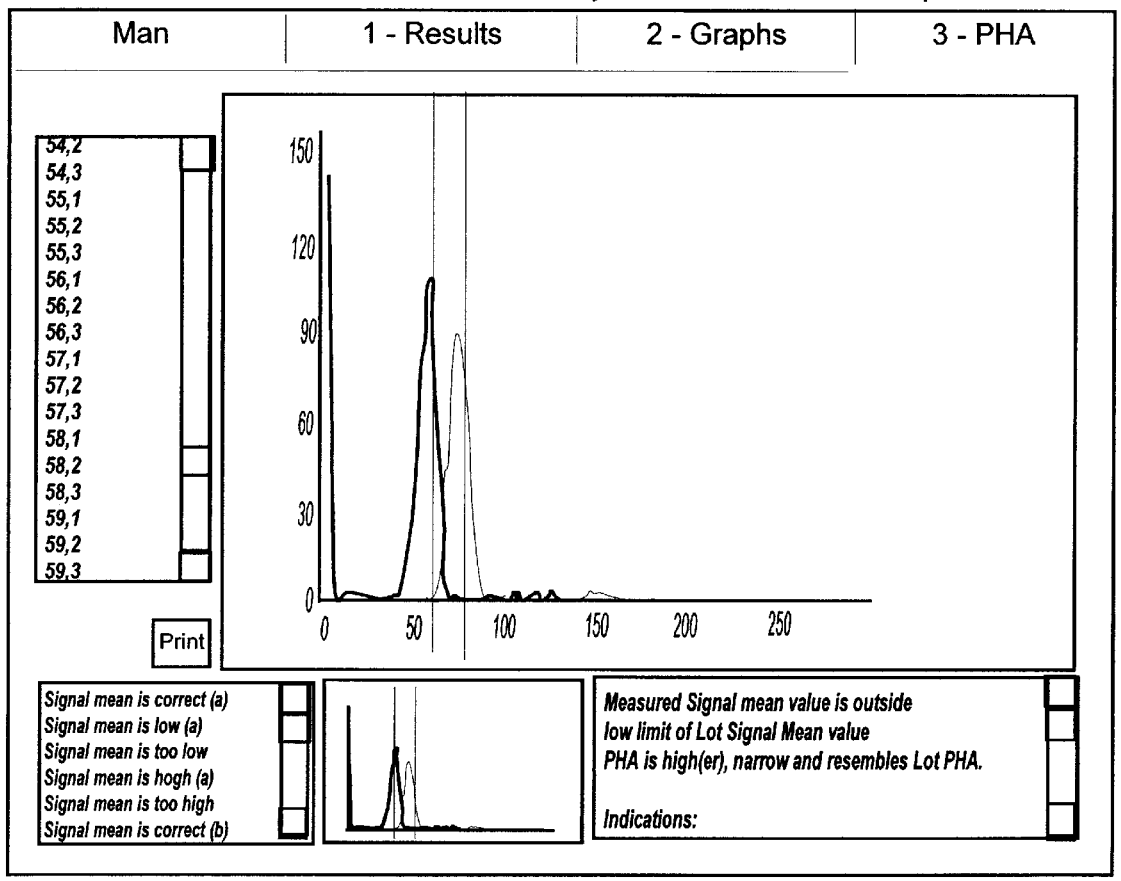
FIG. 10 shows the PHA-diagram for a specific measurement (No 58.2).
FIG. 11 shows a screen print showing the PHA-diagram for a specific measurement (No 58.2) and a theoretical, desired PHA-diagram.

The screen prints shown in FIGS. 9 and 11 may appear a little hazy, and for the sake of clarity all relevant data are presented in tables 1, 2 and 3.

DETAILED DESCRIPTION OF A PREFERRED EMBODIMENT

The invention will be explained in greater details in the following non-limiting example of a preferred embodiment according to the invention.

The Flow Cytometer

Figure 1:
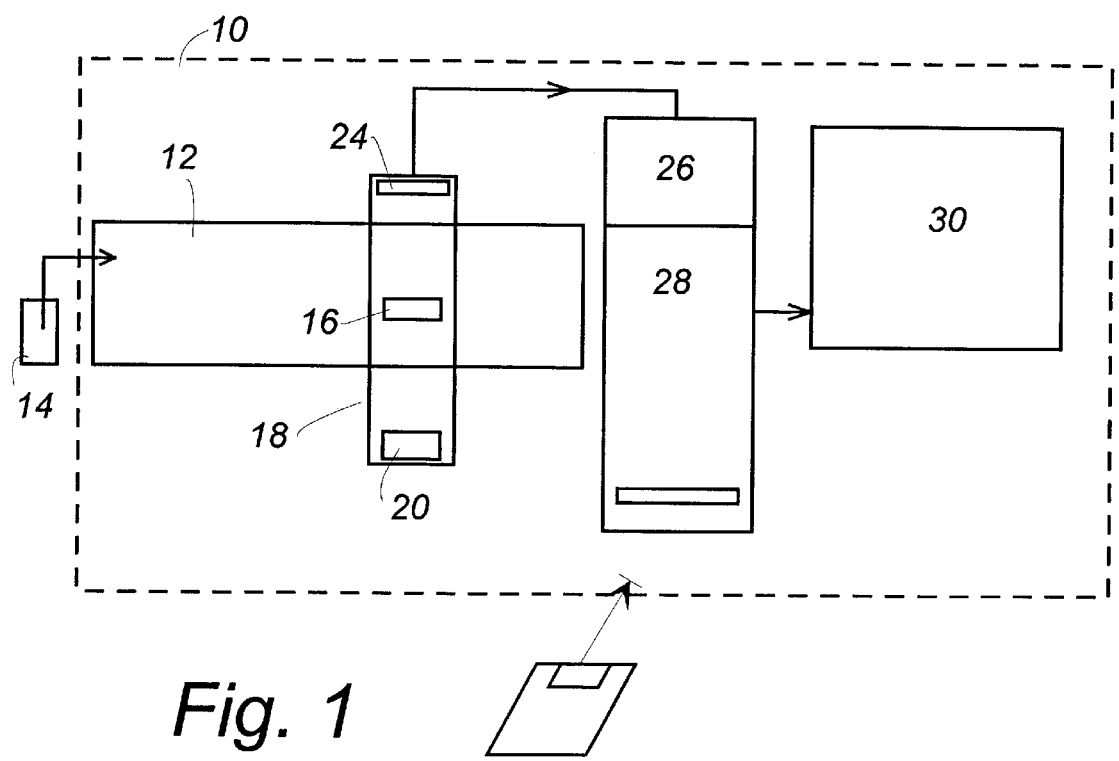
FIG. 1 shows a schematic and simplified diagram of a flow cytometer according to the invention.

A preferred embodiment of a flow cytometer according to the invention is shown schematically in FIG. 1. The flow cytometer 10 comprises a flow system 12 adapted to aspirate a milk sample from a sample cup 14; the flow system is arranged to mix the sample with a fluorescent dye. The flow system includes a transparent cuvette 16 through which a thin string of the milk sample is passing surrounded by a sheath fluid. An optical system 18 includes a light source 20, optics forwarding a light beam, passing through the transparent cuvette 16, hitting the thin string of the milk sample, further optics collecting any fluorescence light emitted by the stained cells in the milk sample passing through the cuvette 16, a photo detector 24 detecting the fluorescence light, i.e. transferring the fluorescence light into electronic signals, and electronic signal and data processing equipment 26. Preferably, the data processing equipment includes a personal computer 28. Further the data processing equipment includes a monitor 30 or similar display unit. The flow cytometer is specifically designed for use in dairies and laboratories analysing milk supplied by farmers.

The features of the method are illustrated schematically in FIG. 16 and explained in details in the following: . . .

The Lot

The user of the flow cytometer receives from the flow cytometer manufacturer or other supplier a so-called "lot", which is a batch of standard samples, i.e. a plurality of small containers filled with a standard fluid. The characteristics of the standard fluid have been duly analysed by the supplier. The presently preferred standard samples comprise 30 ml water, additives and a number of plastic beads, about 6 µm of size. As the plastic beads tend to settle on the bottom of the sample cup, careful shaking of the presently applied standard samples is essential to obtain a good result.

The standard fluid may also be applied for calibration of the flow cytometer, but such use is not the main item of this patent application.

Information on the characteristics of the standard samples of the lot is delivered to the user, preferably on storage means, such as a floppy disk or a CD-ROM, also comprising software providing for analysis of the signals detected and counts obtained by the flow cytometer instrument. The user imports the lot data from the disk to the data processing equipment 26–28 attached to the flow cytometer. Alternatively the standard kit including the lot may comprise means such as a user identification and/or password allowing access to storage means containing the information, e.g. information to be accessed by the internet.

Performance Check and Operation of the Flow Cytometer

Generally, the standard samples are handled and counted in the flow cytometer in the same manner as the ordinary milk samples. Regularly, e.g. about every 2 hours, the user introduces a well shaken standard sample into the flow cytometer. When a portion of the standard sample fluid is aspirated into the flow cytometer it is mixed with a fluorescent dye such as Ethidium Bromide. The flow system 12 incorporates appropriate mixing and time delay means to ensure that some dye has adhered to each cell or particle to be counted. The stained cells or particles pass preferably one by one in a string of sample fluid surrounded by a sheath fluid. A light beam from the optic light source 20 passes across the string of particles thereby initiating the stained particles to fluorescence. Each flash of fluorescence is detected by a highly sensitive photo detector 24 connected to the signal and data processing equipment 26–28 wherein the counting is accomplished.

The Counting and the PHA Diagram

Figure 2:
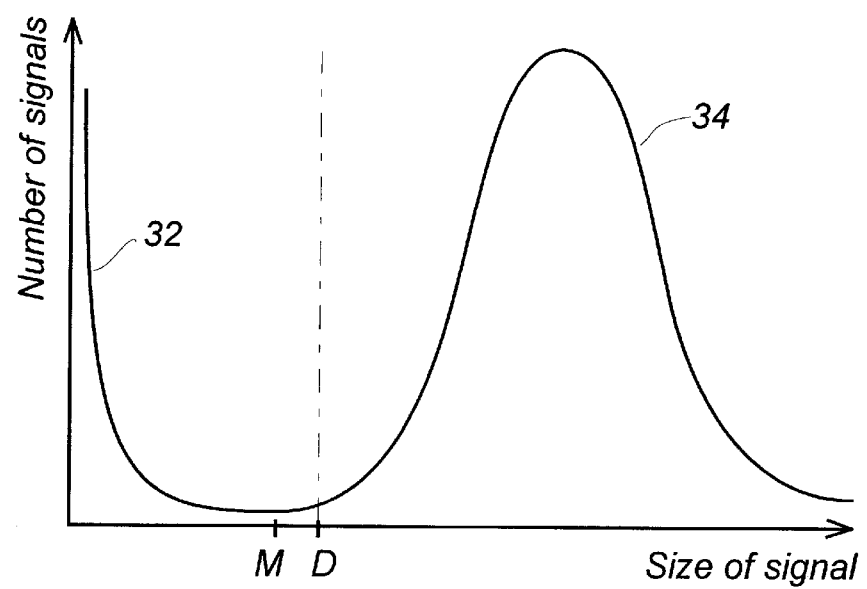
FIG. 2 shows a typical PHA diagram.

The counting of particles can be analysed by use of the so-called PHA-diagram (PHA means Pulse Height Analysis). It is a diagram or histogram showing the number of pulses versus the signal size (height). A typical PHA-diagram is shown in FIG. 2. It appears from the curve section 32 in the diagram that a great number of low-signal pulses are detected. Generally, they indicate noise. The bell formed section 34 (in the middle of the diagram) having a maximum indicates the appearance of higher signals, which are interpreted as being caused by the particles to be counted. The area of said portion indicates the number of particles. The PHA-diagram is very useful for indicating the noise and accordingly enables discrimination of the noise. In a preferred embodiment all signals of a size smaller than an adjustable value D, equal to or close to the minimum M shown in FIG. 2, are considered as noise. All signals of a size greater than D are considered to represent particles and are accordingly counted.

PHA-diagnostics

Figure 3:
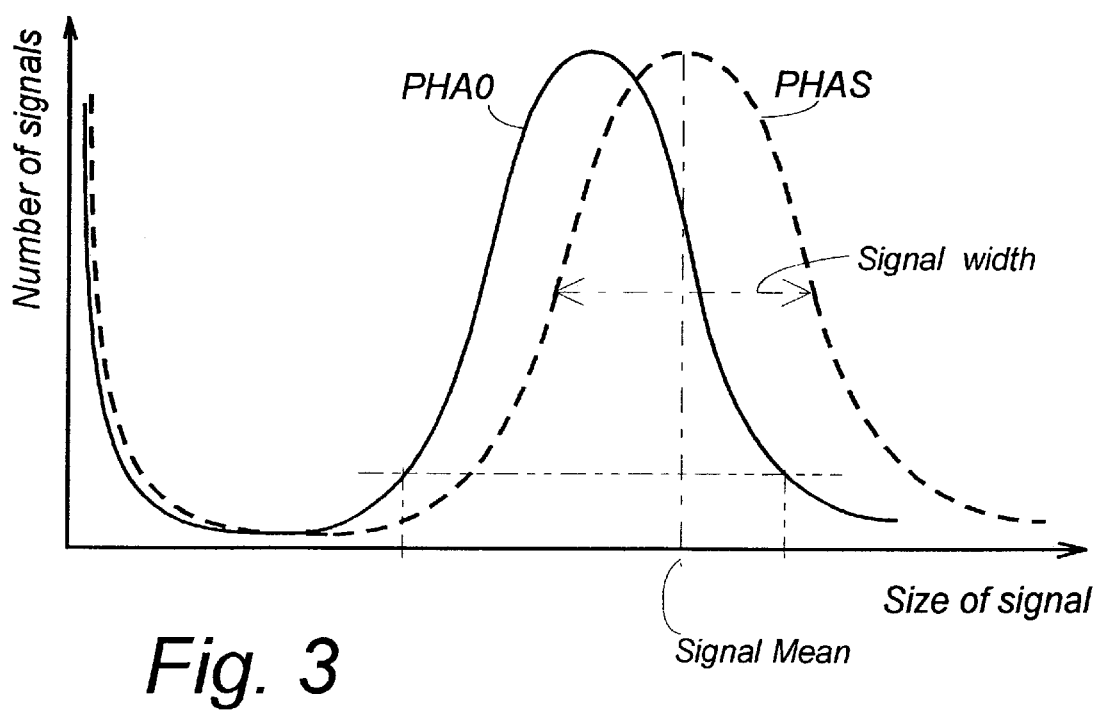
FIG. 3 shows a display of PHA diagrams according to the invention indicating e.g. that gain setting may be a little too high.
Figure 4:
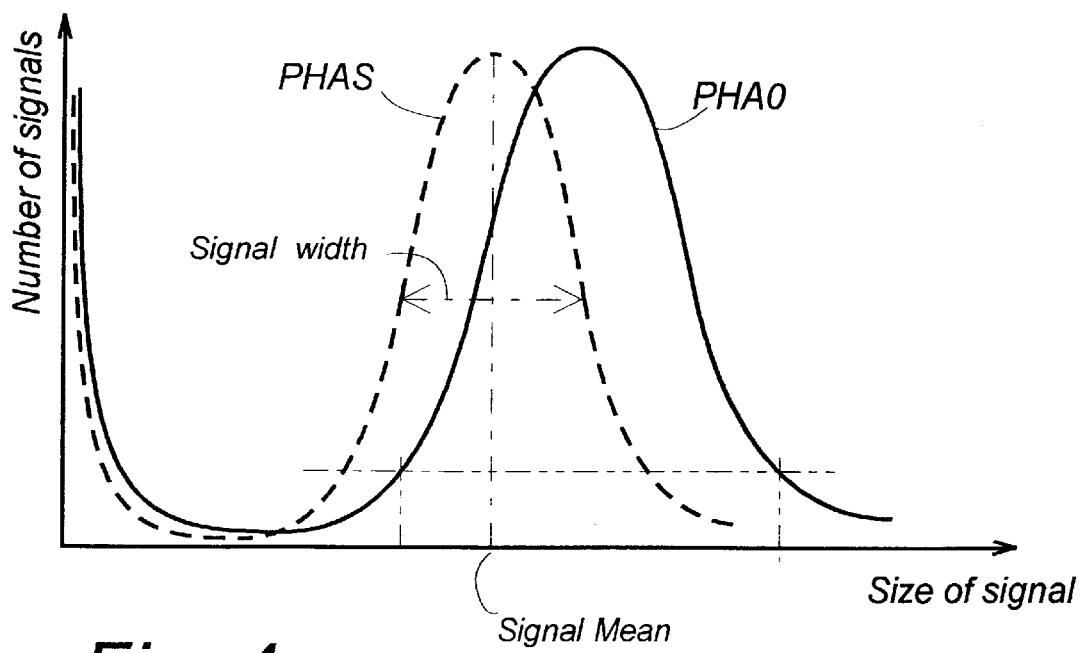
FIG. 4 shows another display of PHA diagrams according to the invention indicating e.g. too high flow rate of sheath fluid.

According to the present invention the PHA-diagram (FIGS. 2, 3, 4) is extremely useful for diagnosing the performance (operation) of the instrument. According to the invention the PHA-diagram (or curve) obtained for the standard sample can be displayed to the user on the attached monitor 30 (or display unit) together with a second PHA-diagram (or curve), PHA0. The second diagram or curve indicates the optimal, (desired=best possible) diagram for the measured lot (the second diagram is obtained from the data supplied on the INFO disk forwarded by supplier together with the lot). If the new PHA-diagram (PHAS= PKA of Standard Sample) obtained for the standard sample covers or is identical (or almost identical) to the optimal diagram PHA0 the operation of the flow cytometer is good. Any difference can be used for diagnosis as explained further in the following. Differences exceeding predefined limits are used as symptoms, indicating poor operation/performance of the flow cytometer. In order to evaluate the differences a Signal Mean is calculated (Gauss mean).

Library

The information supplied by the manufacturer includes a "library" for fault finding. In the library a number of symptoms are related to adequate advices indicating to the user the actions to be taken in order to remedy any poor operation/performance. In a preferred embodiment the library is stored on a disk, preferably a CD-rom or similar high-capacity disk. An example of the stored information is shown on pages 11–14 as table No. 1. The example according to table 1 discloses a presently preferred way of displaying the symptoms and diagnostic recommendations. 14 different situations or so-called "versions" are described in the table. No. 0.0, i.e. the first one, is the perfect case, all values are within limits and close to the optimum. All of the next 13 cases represent indications for some kind of maladjustment. The first column to the left shows the observed symptoms. (In some cases the same symptoms appear in different versions a, b, c). The right column includes the messages provided to the user in the right side window at the bottom of FIG. 10. These messages include: a) further detailed symptoms, b) indications such as possible proposals for diagnosis of what might be the reason for poor performance, and c) what to do to remedy the situation.

Typical symptoms indicating poor performance are: Signal Mean low, Signal Mean too low, Signal Mean much too low, Signal Mean high, Signal Mean too high, PHA is wide, PHA is low, PHA skewed or double, Typical diagnosis may be:

electronic gain too low or too high: needs adjustment of the gain in the electronic signal processing means;

obstructions or clogging in the flow system;

sheath flow too low, too high, or much too high: adjustment of the sample flow rate needed;

incorrect mixing of sample and dye;

defect lamp;

maladjustment of lamp or microscope; needs optical adjustment or alignment of the lamp and/or the microscope;

Preferred embodiment

Figure 16:
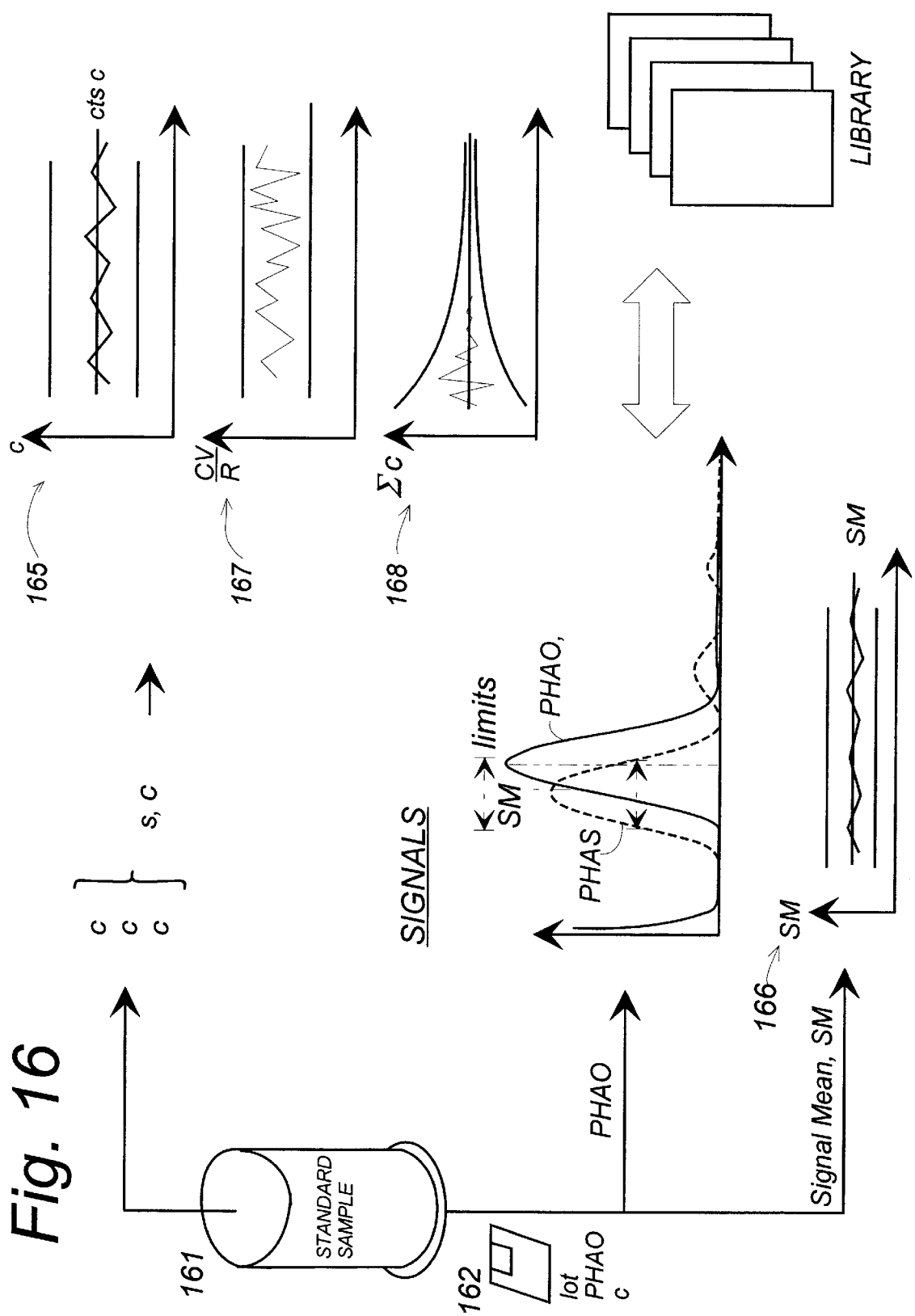
FIG. 16 shows a schematic diagram illustrating the method according to the invention.

The principles of a preferred embodiment of the present invention is shown schematically in FIG. 16. The input to the instrument is a standard fluid sample 161 and an information carrier such as a disk 162, comprising information on the lot and software.

The following actions/operations are carried out:

Every 2 hours a computer prompt tells the user to insert a standard sample 161 (from a lot delivered by the supplier)

the flow cytometer measures the standard sample a plurality of times, e.g. three times, i.e. obtains three counts, $c_1$, $c_2$, $c_3$, each of which represents the number of particles passing by during a predetermined measurement period of a few seconds, e.g. 2 sec, (preferably, a period according to normal operation mode of the instrument). The count is assigned a consecutive record or registration number, e.g. No 58.1, 58,2, 58.3, 59.1 . . .

Figure 5:
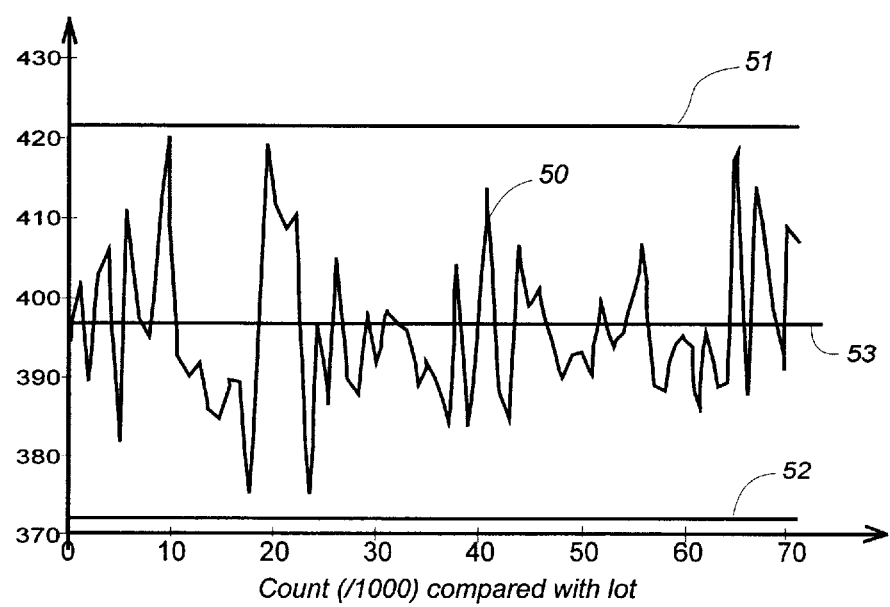
FIG. 5 shows a diagram indicating the variation of counts compared with lot count.
Figure 8:
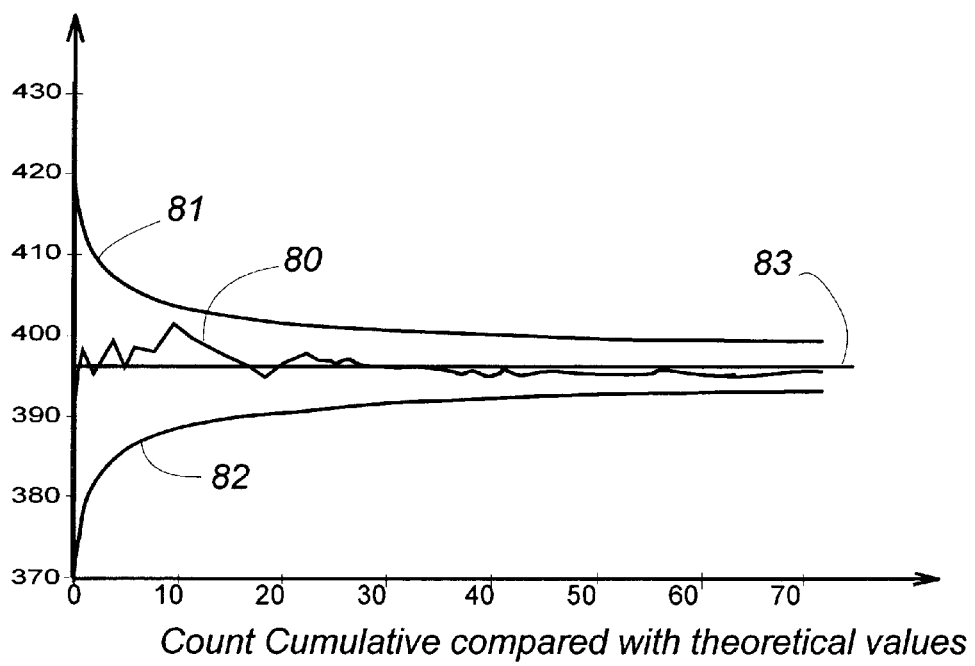
FIG. 8 shows a cumulative mean count compared with theoretical values (Count Cumulative).

The data processing equipment including appropriate software calculates the number of particles $c_1$, $c_2$, $c_3$ the mean count, $c=(c_1+c_2+c_3)/3$, (count in FIG. 5, also shown as 165 in FIG. 16)

the signal size the mean signal size (Signal Mean in FIG. 6), and the standard deviation is calculated from the three measurements, $$s=\sqrt{((c_1-c)^2+(c_2-c)^2+(c_3-c)^2)/2}$$ —or the Coefficient of Variation: $100\%*s/c$ (CV is shown in FIG. 7, compared with theoretical CV that is calculated according to Poisson sampling statistics); also shown as 167 in FIG. 16;

an accumulated mean value of all counts obtained by the instrument:

$\Sigma c_1$, (Count Cumulative in FIG. 8 and 168 in FIG. 16)

The calculated results are compared to the information delivered with the lot (by the supplier of the lot) including upper and lower optimal operating limits (reference numbers 51, 52, . . . in FIGS. 5–8) (e.g. mean signal size, count, CV), and comments to each measurement and mean results are displayed to the user e.g. as shown in the list of results in FIG. 9, in order to draw the operator's attention to any poor performance. For the sake of clarity, extracts from the list of results are redisplayed in table 3.

On request the data processing equipment (with appropriate software) of the flow cytometer displays a PHA-diagram on the attached monitor 30 indicating the signal size.

Each count (ref. number 50 I FIG. 5) is compared to the Lot count $c_0$ (53), which is a count number supplied with the lot and representing the actual number of particles in the present lot. Accordingly, the present count ideally should equal the lot count (53). Lot limits (51, 52) indicating admissible variations are also supplied with the lot. FIG. 5 shows the count (50) compared with lot count (53) for a plurality of standard samples 0–72. The horizontal axis indicates the registered sample No. and the vertical axis indicates the count per 1000 particles. The allowable variations are indicated by upper and lower lot limits (51, 52) . In the present case the lot count/1000 is 396 and the limits (51, 52) are set to 371 and 421. The bold line or track (50) indicates the actual counts/1000 found. They appear to be within the limits (51, 52).

Figure 6:
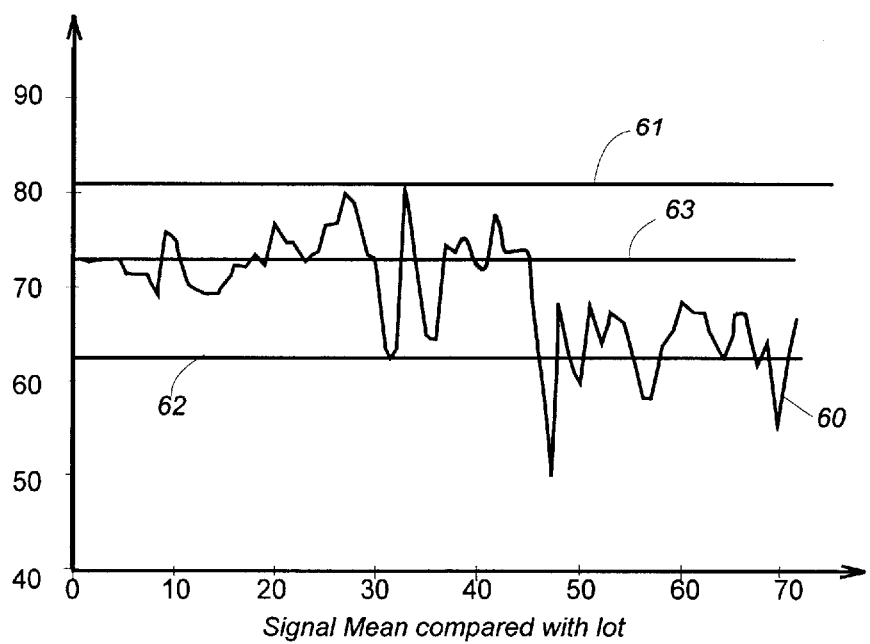
FIG. 6 shows a diagram indicating the signal mean compared with lot.
Figure 7:
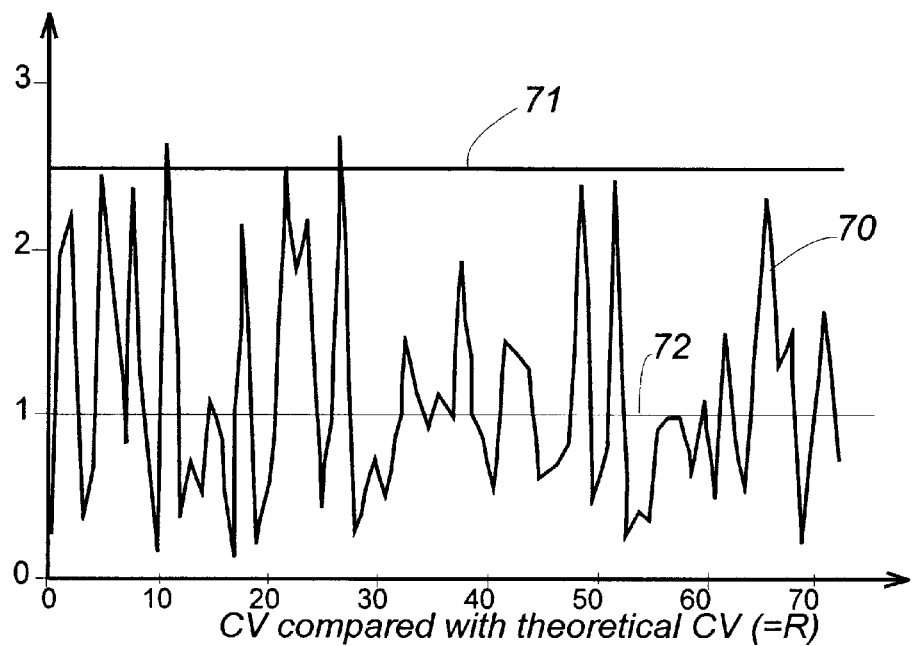
FIG. 7 shows the standard deviation or Coefficient of Variation, CV, compared with theoretical CV.

FIG. 6 shows a Signal Mean (60) compared with a lot signal (63) and upper and lower limits (61, 62). In order to illustrate (as an example) a possible failure or defect, the attention is drawn to sample No 48: A significant decrease in signal seems to appear after sample No. 48. When comparing to the detailed result it appears that somehow the gain was decreased from 625 to 615.

FIG. 7 shows as an example a sequence of calculated CV/R (ref. number 70 I FIG. 7) compared with the theoretical value: CV/R=1 (72). An upper limit (71) indicates the admissible variation.

FIG. 8 shows a Count Cumulative (80) compared with theoretical values. The accumulated mean value is compared to curved limits (81, 82) (which are p% confidence limits) confining a gap getting narrower as the sample number increases. However, a batch of samples (so-called "lot") has a limited number of samples and a new lot may have a different number of particles per ml. In order to avoid a displacement of all the predefined values, e.g. the theoretical mean, (the so-called lot count), and the limits, it is preferred that the accumulated mean value (80) and the limits (81, 82) are normalised, i.e. divided by the Lot Number, a lot mean count in order to allow for continuous watch, also when the lot is changed.

EXAMPLE

When the user gets a message or remark, e.g. as indicated in table 1 for the records 19, 49, 51, 58 and 59, he should as soon as possible study the latest measurement results. The software is "windows®"-based, providing for display of several "windows". FIG. 9 shows a list of "check measurements" or results of the same kind shown in table 3. The highlighted sample No. 58 has got a remark. Accordingly, the user has asked for a display of "Result details for 58". The result details are displayed in table form (also shown in table 2 page 15) including six rows (comprising the three measurements (rep 1, rep2, rep3), an average value, CV% (a theoretical standard deviation), and the lot average), and eight columns (comprising the values found for the count, R, Signal Mean, (58), Signal Width (8), Z (a value which quantifies the discriminating space (separation) between noise and signals), Discriminator, Noise Level, and Remarks). In a third window the lot data are displayed. Further, the display facilities allow for the display of a measured PHA-diagram and a theoretical, desired PHA-diagram (FIG. 10). A print-out of the displayed PHA-diagrams is shown in FIG. 11. As it appears from the screen print in FIG. 10, the user may select any registered measurement, e.g. No 58.2, which is stored in the data storage means as a sequence of numbers, comprising the ordinates for the PHA-curve obtained for No 58.2. The PHA-curve is displayed with the optimal PHA-curve. It is obvious that the signal Mean is too low (cf. FIG. 6). The bottom section of the display comprises three small adjacent windows, a left window in which the symptom "Signal Mean is too low" is highlighted, a centre window showing the symptomatic picture of the PHA-curves, and a right-side window showing details of symptoms and indications, comprising recommendations for how to remedy the poor performance. Further examples of symptoms and recommendations are shown in table 1 on pages 11–14. In the below table "QCHECK LIBRARY" is a short notation for Quality check library.

Figure 12:
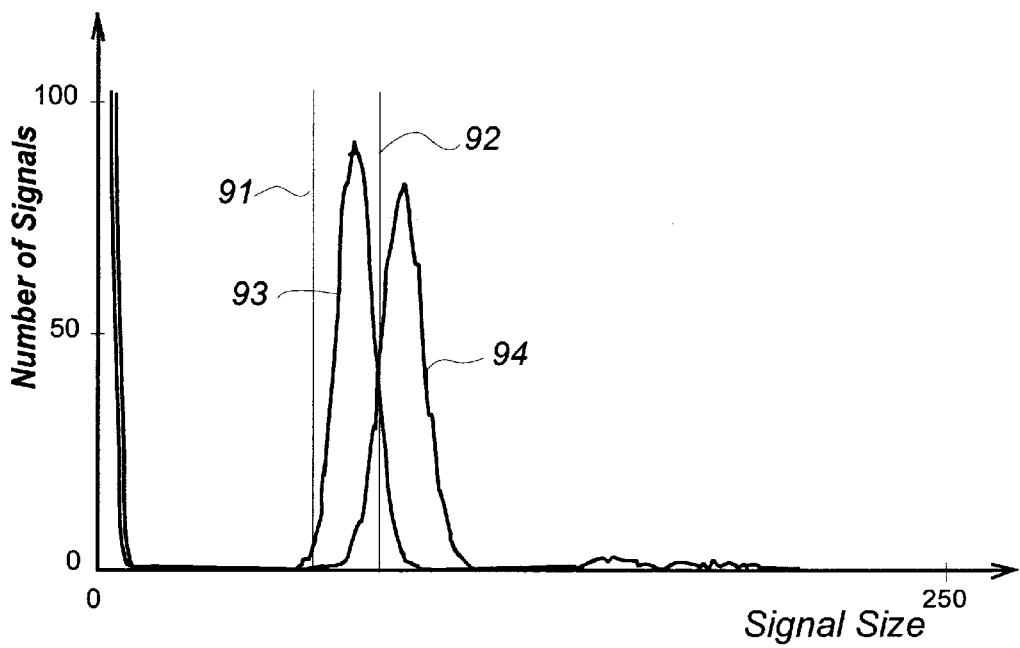
FIG. 12 shows a plot of a PHA-diagram for a first specific situation.
Figure 14:
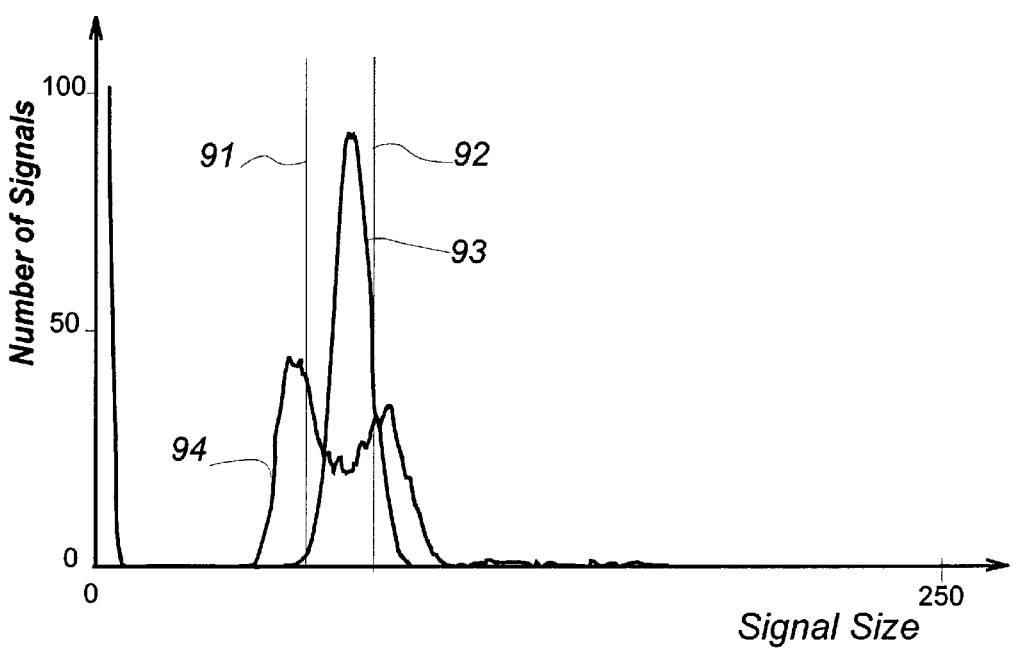
FIG. 14 shows a plot of a PHA-diagram for a third specific situation.
Figure 13:
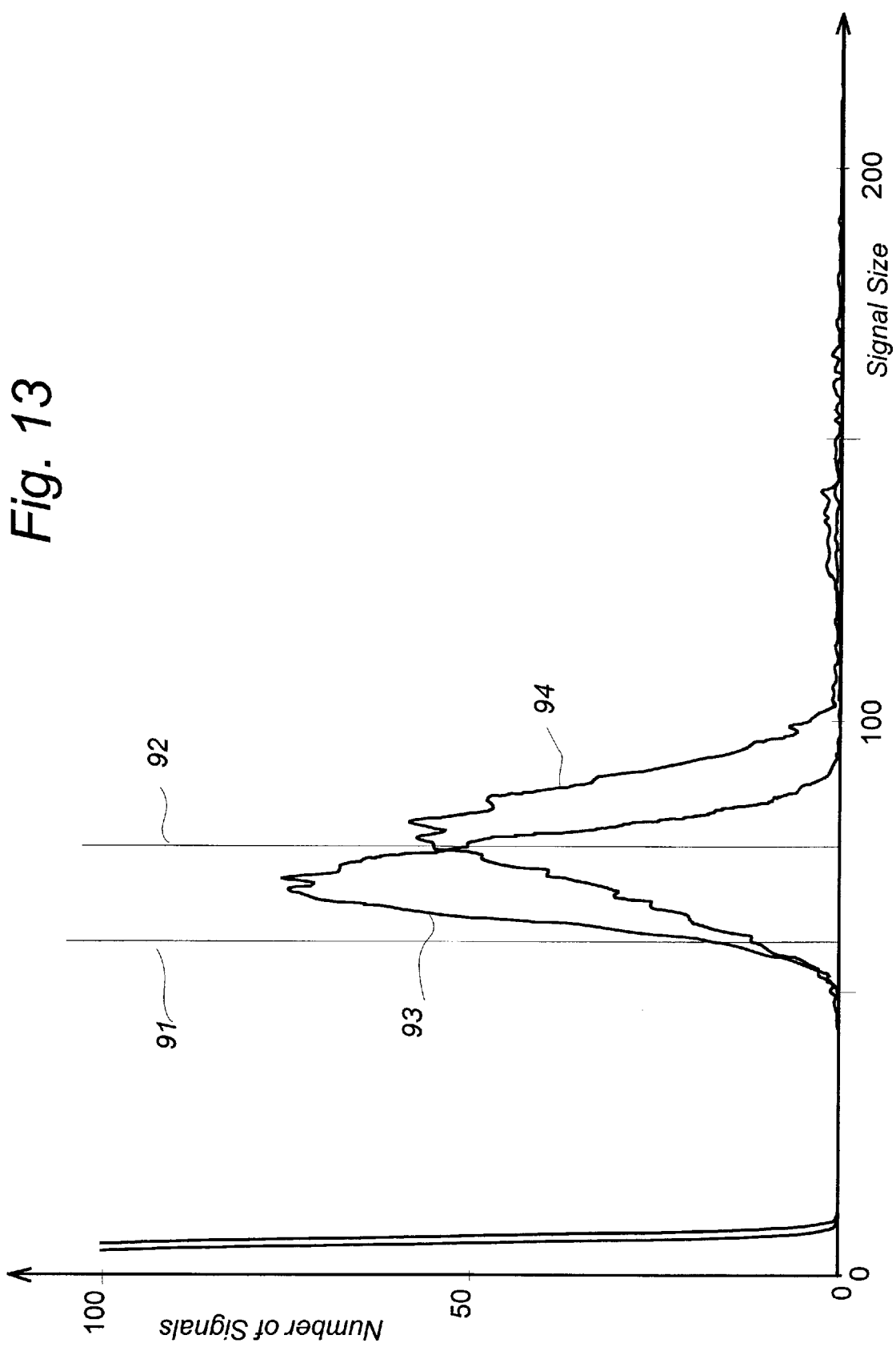
FIG. 13 shows a plot of a PHA-diagram for a second specific situation.

FIGS. 12–14 show as examples PHA-diagrams for various situations. The vertical lines 91 and 92 are lower and upper lot limits for PHA for the measured FMA-sample. The grey PHA curve 93 shows how the PHA ideally should look, the dark curve 94 shows the curve of the actually measured sample.

The PHA-diagram of FIG. 12 illustrates a situation characterised in that the Signal Mean is too high. Measured Signal Mean Value is outside high limit of lot signal Mean Value. PHA is high, narrow and resembles Lot PHA. The indications relating to this situation are: Gain setting may be too high, check gain in result list, changed? Sheath flow may be low. Has sheath flow been reduced? check. If flow is OK: reduce gain.

The PHA-diagram of FIG. 13 illustrates a situation characterised in that the Signal Mean is high, PHA is wide. Measured Signal Mean Value may be within or outside limit, and higher than lot signal Mean Value. PHA is lower and wider than Lot PHA. The indications relating to this situation are:

Sheath flow may be low. Has sheath flow been reduced? check. Reset flow to 10–10.5 ml/min at earliest convenience. Finally set gain correctly (i.e. Measured Signal Mean shall be close to Lot Signal Mean +/−2).

The PHA-diagram of FIG. 14 illustrates a situation characterised in that the PHA is skewed or double. Measured Signal Mean Value may be within or outside limit of lot signal Mean Value. PHA is skewed or double, lower and wider than Lot PHA. The indications relating to this situation are: 1) Microscope adjustment is not OK 2) Sheath flow may not be correct Check sheath flow and reset if necessary to 10–10.5 ml/min. Readjust microscope gently for narrow and high PHA and max signal mean. Finally set gain correctly (Measured Signal mean is close to Lot Signal Mean +/−2).

It appears from the above examples that the method according to the present inventions allows the user himself to perform many ordinary adjustments of the instrument Thus it is ensured that the instrument will operate at perfect performance substantially all the time.

TABLE 1

EXPLANATIONS IN QCHECK LIBRARY PER 15 AUG. 1997

| HEADER | DESCRIPTIONS |
|---|---|
| Signal Mean is correct (a) | Measured Signal Mean Value is within limits and close to Lot Signal Mean Value. PHA is high, narrow and resembles Lot PHA. Indications: |
| | (1) Gain setting is OK<br>(2) Sheath flow is OK.<br>(3) Microscope adjustment is Ok.<br>(4) Lamp is OK.<br>(5) No obstructions in flow cell.<br>Note: If measured PHA is narrow and positioned correctly then it is of no significance if measured PHA is a little lower or higher than Lot PHA (Ver. 0.0) |
| Signal Mean is low (a) | Measured Signal Mean Value is within limits but lower than Lot Signal Mean Value. PHA is high, narrow and resembles Lot PHA. Indications: |
| | (1) Gain setting may be a little low. Check gain in result List. Changed?<br>(2) Sheath flow may be high. Has sheath flow been increased? Check.<br>(3) Lamp alignment may be disturbed.<br>What to do: No urgent adjustments. If flow is OK (9.5–10.5 ml/min.): Watch for any further changes the following days.<br>When appropriate: Increase gain to correct setting (Measured Signal Mean is close to Lot Signal Mean, ±2). (Ver. 1.0) |
| Signal mean is too low | Measured Signal Mean Value is outside low limit of Lot Signal Mean value. PHA is high(er), narrow and resembles Lot PHA. Indications: |
| | (1) Gain setting may be too low. Check gain in result List. Changed?<br>(2) Sheath flow may be much too high. Has sheath flow been increased? Check.<br>(3) Lamp may have failed.<br>What to do: Find problem at your earliest convenience. If gain is unchanged and flow is OK (9.5–10.5 ml/min.): Realign lamp for maximum Signal Mean Value or replace lamp. Finally set gain correctly (Measured Signal Mean is close to Lot Signal Mean, ±2). (Ver. 2.0) |
| Signal mean is high (a) | Measured Signal Mean Value is within limits but higher than Lot Signal Mean Value. PHA is high, narrow and resembles Lot PHA. Indications: |
| | (1) Gain setting may be a little high. Check gain in result List. Changed?<br>(2) Sheath flow may be low. Has sheath flow been reduced? Check.<br>What to do: No urgent adjustments. When appropriate: If flow is OK (9.5–10.5 ml/min.) gain is reduced to correct setting, i.e. Measured Signal Mean is close to Lot Signal Mean, ±2. (Ver. 3.0) |

TABLE 1-continued

EXPLANATIONS IN QCHECK LIBRARY PER 15 AUG. 1997

| HEADER | DESCRIPTIONS |
| --- | --- |
| Signal mean is too high | Measured Signal Mean Value is outside high limit of Lot Signal Mean Value. PHA is high, narrow and resembles Lot PHA.<br>Indications:<br><br>(1) Gain setting may be too high. Check gain in result List. Changed?<br>(2) Sheath flow may be low. Has sheath flow been reduced? Check.<br>What to do: Find problem at your earliest convenience. If flow is OK (9.5–10.5 ml/min.) gain is reduced to correct setting, i.e. Measured Signal Mean is close to Lot Signal Mean, ±2. (Ver. 4.0) |
| Signal Mean is correct (b) | Measured Signal Mean Value is within limits and close to Lot Signal Mean Value. PHA is high, narrow and resembles Lot PHA.<br>See also: "Signal Mean is correct (a)". This is an example of measured PHA a little lower than Lot PHA.<br>Variations in PHA-heights - insignificant to milk measurements - may be caused by minor differences in optics, lamp and microscope adjustments. (Ver. 5.0) |
| Signal Mean is high (b) | Measured Signal Mean Value is within limits but higher than Lot Signal Mean Value. PHA is high, narrow and resembles Lot PHA.<br>Indications:<br><br>(1) Gain setting may be a little high. Check gain in result List. Changed?<br>(2) Sheath flow may be low. Has sheath flow been reduced? Check.<br>(3) Microscope may need adjustment<br>What to do: If flow is not OK: Repair problem at your earliest convenience. Increase flow to 9.5–10.5 ml/min. Check or readjust microscope gently for max. Signal Mean. Finally set gain correctly, i.e. Measured Signal Mean is close to Lot Signal Mean, ±2. (Ver. 6.0) |
| Signal Mean high, PHA wide | Measured Signal Mean Value may be within or outside limit and higher than Lot Signal Mean Value. PHA is lower and wider than Lot PHA.<br>Indications:<br><br>(1) Sheath flow may be low. Has sheath flow been reduced? Check.<br>What to do: Reset flow to 9.5–10.5 ml/min. at your earliest convenience. Finally set gain correctly, i.e. Measured Signal Mean is close to Lot Signal Mean, ±2. (Ver. 7.0) |
| Signal Mean is low (b) | Measured Signal Mean Value is within limits but lower than Lot Signal Mean Value. PHA is high, narrow and resembles Lot PHA.<br>Indications:<br><br>(1) Gain setting may be a little low. Check gain in result List. Changed<br>(2) Sheath flow may be high. Has sheath flow been increased? Check.<br>(3) Lamp alignment may be disturbed.<br>(4) Microscope may need adjustment.<br>What to do: If flow is not OK: Repair problem at your earliest convenience. Reduce flow to 9.5–10.5 ml/min. Check or readjust microscope gently for maximum Signal Mean. Finally set gain correctly, i.e. Measured Signal Mean is close to Lot Signal Mean, ±2. (Ver. 8.0) |
| Signal Mean is low (c) | Measured Signal Mean Value is within limits but lower than Lot Signal Mean Value. PHA is high, narrow and resembles Lot PHA.<br>Indications:<br><br>(1) Gain setting may be a little low. Check gain in result List. Changed?<br>(2) Sheath flow may be high. Has sheath flow been increased? Check.<br>What to do: If flow is not OK: Repair problem at your earliest convenience. Reduce flow to 9.5–10.5 ml/min. Finally set gain correctly, i.e. Measured Signal Mean is close to Lot Signal Mean, ±2. (Ver. 9.0) |
| PHA low, wide | Measured Signal Mean Value may be within or outside low limit of Lot Signal Mean Value. PHA is skewed, lower and wider than Lot PHA.<br>Indications:<br><br>(1) Microscope adjustment is not OK.<br>What to do: Repair problem at your earliest convenience. Check that gain is OK; do not change it. Check that flow is OK, 9.5–10.5 ml/min. Readjust microscope gently to obtain narrow and high PHA and a maximum Signal Mean Value. Finally set gain correctly, i.e. Measured Signal Mean is close to Lot Signal Mean, ±2. (Ver. 12.0) |
| PHA skewed or double | Measured Signal Mean Value may be within or outside low limit of Lot Signal Mean Value. PHA is skewed/double, lower and wider than Lot PHA.<br>Indications:<br><br>(1) Microscope adjustment is not OK.<br>(2) Sheath flow may not be correct.<br>What to do: Repair problem at your earliest convenience. Check sheath flow and reset if necessary to 9.5–10.5 ml/min. Readjust microscope gently to obtain narrow |

TABLE 1-continued

EXPLANATIONS IN QCHECK LIBRARY PER 15 AUG. 1997

| HEADER | DESCRIPTIONS |
|---|---|
| | and high PHA and a maximum Signal Mean Value. Finally set gain correctly, i.e. Measured Signal Mean is close to Lot Signal Mean, ±2. (Ver. 13.0) |
| Signal Mean is much too low | Measured Signal Mean Value is outside limit of Lot Signal Mean Value. PHA is high, narrow and resembles Lot PHA.<br>Indications:<br><br>(1) Gain setting may be a little low. Check gain in result List. Changed?<br>(2) Sheath flow may be much too high. Has sheath flow been increased? Check.<br>(3) Microscope may be maladjusted.<br>(4) Lamp alignment or replacement may be needed.<br>What to do: Repair problem at your earliest convenience. Check and reset flow if necessary to 9.5–10.5 ml/min. Adjust lamp to maximum DC-level on milk sample. Adjust Microscope gently to maximum on DC-level on milk sample. Fine tune microscope very gently to max. Signal Mean Value with FMA sample. Finally set gain correctly, i.e. Measured Signal Mean is close to Lot Signal Mean, ±2. If gain has to be increased significantly: Replace lamp. (Ver. 14.0) |

In a specifically advantageous embodiment of the present invention the registered data and/or provided parameters may be transferred by a modem and attached communication means to a service centre at a supplier or manufacturer, who in return may provide recommendations for remedying the defect and/or send corrective messages controlling the settings of the apparatus. In this way also difficult cases in which the user would tend to ask for the visit of a service engineer may be taken care of by remote control.

Compensation for Agglomeration of Particles in the Standard Sample

The PHA diagram further provides for a compensation for agglomeration of particles in the standard sample. Experience has shown that occasionally the standard samples may include some particles which have agglomerated two by two into doublets, or three by three into triplets. The bigger particles, the bigger signals. Accordingly, the PHA-diagram may look as indicated in FIG. 15.

The first top (101) represents single particles (singlets) in a number of 1166; the second top (102) represents double particles (doublets) in a number of 429, and the third top (103) represents triplets in a number of 77. Accordingly the program, i.e. the software controlling the instrument and evaluating the measurements may be arranged to compensate for the agglomerated particles by adding the doublets and triplets twice and three times, respectively.

The formation of doublets and triplets (and possibly other multiple) is believed to depend on the age of the particles, the shaking of the sample as well as the temperature of the sample. It is difficult to predict the amount of doublets and triplets in the standard samples and accordingly the above method of compensation solves a current problem.

It is obvious to people skilled in the art that embodiments according to the invention and described above may be varied in several ways within the scope of protection as defined in the following patent claims.

TABLE 2

Result details for 58

| | Count | R | Signal Mean | Signal Width | Z | Discriminator | Noise Level | Remarks |
|---|---|---|---|---|---|---|---|---|
| rep 1 | 418 | 2.67 | 58 | 8 | 3.3 | 29 | 4 | signal low |
| rep 2 | 399 | 2.74 | 58 | 8 | 3.4 | 28 | 4 | signal low |
| rep3 | 399 | 2.73 | 58 | 8 | 3.7 | 25 | 4 | signal low |
| Average | 405 | 2.71 | 58 | 8 | 3.4 | 27 | 4 | signal low |
| CV(%) | 271 | | 0.0 | | | | | |
| Lot Average | 396 | 2.75 | 73 | | | | | 7144511 |

Fossomatic Quallty Check - Results

| No. | Date | Time | Count | CV | R | Signal Mean | CV | Signal Width | Remarks | Lot No | Gain |
|---|---|---|---|---|---|---|---|---|---|---|---|
| 1 | June 6, 1997 | 12:36:15 | 393 | 0.83 | 2.76 | 73 | 0.0 | 8 | OK | 7144511 | 622 |
| 2 | June 6, 1997 | 12:37:30 | 402 | 5.45 | 2.73 | 73 | 0.0 | 8 | OK | 7144511 | 622 |

-continued

Fossomatic Quality Check - Results

| No. | Date | Time | Count | CV | R | Signal Mean | CV | Signal Width | Remarks | Lot No | Gain |
|---|---|---|---|---|---|---|---|---|---|---|---|
| 3 | June 6, 1997 | 12:37:51 | 389 | 6.20 | 2.77 | 73 | 0.8 | 8 | OK | 7144511 | 622 |
| . | | | | | | | | | | | |
| . | | | | | | | | | | | |
| . | | | | | | | | | | | |
| 19 | June 6, 1997 | 17:01:28 | 374 | 6.16 | 2.83 | 72 | 0.8 | 9 | a remark | 7144511 | 625 |
| 20 | June 6, 1997 | 17:02:21 | 390 | 0.70 | 2.77 | 73 | 0.0 | 8 | OK | 7144511 | 625 |
| 21 | July 7, 1997 | 08:38:22 | 419 | 1.19 | 2.67 | 72 | 0.0 | 8 | OK | 7144511 | 625 |
| . | | | | | | | | | | | |
| . | | | | | | | | | | | |
| . | | | | | | | | | | | |
| 48 | July 10, 1997 | 14:33:30 | 400 | 1.93 | 2.73 | 64 | 0.9 | 8 | OK | 7144511 | 625 |
| 49 | July 10, 1997 | 16:17:36 | 394 | 2.28 | 2.75 | 49 | 1.2 | 8 | signal low | 7144511 | 615 |
| 50 | July 10, 1997 | 17:34:39 | 389 | 6.69 | 2.77 | 68 | 0.0 | 8 | OK | 7144511 | 615 |
| 51 | July 11, 1997 | 11:02:47 | 391 | 1.35 | 2.76 | 62 | 2.5 | 8 | signal low | 7144511 | 615 |
| . | | | | | | | | | | | |
| . | | | | | | | | | | | |
| . | | | | | | | | | | | |
| 57 | July 15, 1997 | 06:51:50 | 398 | 2.47 | 2.74 | 62 | 0.9 | 8 | OK | 7144511 | 615 |
| 58 | July 15, 1997 | 08:52:45 | 405 | 2.71 | 2.71 | 58 | 0.0 | 8 | signal low | 7144511 | 615 |
| 59 | July 15, 1997 | 10:54:27 | 388 | 2.69 | 2.77 | 58 | 1.0 | 8 | signal low | 71445i1 | 615 |

What is claimed is:

1. A method of checking the performance of a flow cytometer instrument (10), in which flow cytometer instrument the number of particles or cells in a fluid flow are counted by providing data representing a PHA diagram (Pulse Height Analysis) of registered pulses, the method comprising the steps of:

providing a lot of standard samples, having a standard fluid, including only one type of substantially uniform microbeads, providing optimal data representing an optimal (desired) PHA diagram (PHA0) of the pulses registered, when measuring a standard sample from said lot on a reference flow cytometer instrument, said optimal data representing an optimal (desired) PHA diagram (PHA0) being stored in one of the means of the group consisting of: a memory in the flow cytometer instrument to be checked (10) itself, a memory in data processing means connected to the flow cytometer instrument to be checked (10), means from which the optimal data may be imported into the flow cytometer instrument to be checked (10), and means from which the optimal data may be imported into a data processing means connected to the flow cytometer instrument to be checked (10), measuring a standard sample on the flow cytometer instrument (10) to be checked, providing sample data representing a PHA diagram (PHAS) for the pulses registered during the measurement of the standard sample on the flow cytometer instrument (10) to be checked, comparing the sample data to the stored optimal data, and analysing and/or evaluating said sample data and stored optimal data in order to determine any poor or faulty operation of the flow cytometer instrument to be checked.

2. The method according to claim 1, wherein a standard sample is measured at least three times in the flow cytometer instrument to be checked, and wherein the steps of comparing and analysing comprises the steps of:

processing the sample data representing PHA diagrams (PHAS) so as to calculate and/or provide a number of parameters selected from the group consisting of:

a particle count,
a plurality of particle counts on the same sample,
a mean count,
a standard deviation s and/or Coefficient of Variation CV, based on repeated/consecutive measurements on the same sample and substantially at the same time,
a signal mean value,
a signal width (width of the bell-curve in the PHA-diagram), providing optimal values of corresponding parameters for the standard sample of the standard fluid measured on the reference flow cytometer instrument, comparing the selected parameters for the actual measurement of the standard sample to the optimal values of corresponding parameters of the standard fluid when measured on the reference flow cytometer instrument, analysing said data representing actual parameters and optimal parameters to estimate whether the flow cytometer instrument to be checked is operating substantially optimally, or is not operating substantially optimally, registering any off-limit deviations from optimal operation.

3. The method according to claim 2, wherein the microbeads are unstained until they are applied in the flow cytometer instrument to be checked (10).

4. The method according to claim 2, wherein registered off-limit deviations are considered as symptoms which are indicated to the user.

5. The method according to claim 4, wherein a symptom indicated to the user is associated with a proposal for remedying the defect, expected to generate the symptom.

6. The method according to claim 2, wherein the provided data and/or provided parameters are transferred by a modem and communication means to a service centre at a supplier or manufacturer, who in return may provide recommendations for remedying the defect and/or send corrective messages controlling the settings of the flow cytometer instrument to be checked (10).

7. The method according to claim 1, further comprising the steps of analysing the PHA diagram (PHAS) of the measured standard sample in order to observe any agglomerated microbeads in the measured standard sample, and if PHA diagram reveals further maxima for signals sized above the first bell-formed area comprising a first maximum, adjusting the number of microbeads calculated from the area of the first maximum in the PHA diagram (PHAS) using calculations of the number of microbeads represented by an adjacent, second area of a second maximum in the PHA diagram by adding twice the number of microbeads calculated in the second area to the number of microbeads calculated in the first area.

8. The method according to claim 7, wherein the number of microbeads calculated from the areas of the first and second maxima in the PHAS diagram is adjusted using calculations of the number of microbeads represented by an adjacent, third area of a third maximum in the PHAS diagram by adding three times the number calculated in the third area to the number calculated in the first and second area.

9. The method according to claim 2, characterised by providing an accumulated mean value (80), and curved limits (81, 82) (which are p% confidence limits) confining a gap getting narrower as the sample number increases.

10. The method according to claim 9, wherein the accumulated mean value (80) and the limits (81, 82) are normalised, divided by the Lot Number ($c_0$) being a lot mean count.

11. The method of claim 1, further comprising the step of providing a standard kit comprising a standard fluid including a plurality of substantially uniform microbeads and further comprises associated data means for accessing data representing information on the characteristics of the standard fluid and specifically the content of microbeads.

12. The method of claim 11, wherein the step of providing a standard kit includes using unstained microbeads.

13. The method of claim 11, further comprising the step of delivering the fluid as a batch of standard samples in a plurality of containers of prescribed size comprising a prescribed volume, the fluid comprising water, additives and a number of plastic beads, and that associated data means include information on the number of plastic beads in the fluid.

14. The method of claim 11, further comprising the step of accessing information on the characteristics of the standard samples, as well as information comprising a library of symptoms indicating poor performance and recommendations for how to remedy any poor performance, and/or any precautions to be taken.

* * * * *